(12) United States Patent
Li et al.

(10) Patent No.: US 9,949,644 B2
(45) Date of Patent: Apr. 24, 2018

(54) TORSIONAL VIBRATION RESONANCE FREQUENCY MEASUREMENT METHOD FOR ESTIMATING STABILITY OF DENTAL IMPLANT AND NOVEL AMPLITUDE TRANSFORMER

(71) Applicant: THE FOURTH MILITARY MEDICAL UNIVERSITY OF CHINESE PEOPLE'S LIBERATION ARMY, Xi'an, Shaanxi (CN)

(72) Inventors: Dehua Li, Shaanxi (CN); Yulong Tang, Shaanxi (CN); Bing Li, Shaanxi (CN)

(73) Assignee: Fourth Military Medical University of Chinese People's Liberation Army (CN)

( * ) Notice: Subject to any disclaimer, the term of this patent is extended or adjusted under 35 U.S.C. 154(b) by 14 days.

(21) Appl. No.: 14/916,391

(22) PCT Filed: Sep. 1, 2014

(86) PCT No.: PCT/CN2014/000811
§ 371 (c)(1),
(2) Date: Mar. 3, 2016

(87) PCT Pub. No.: WO2015/032171
PCT Pub. Date: Mar. 12, 2015

(65) Prior Publication Data
US 2016/0206201 A1 Jul. 21, 2016

(30) Foreign Application Priority Data
Sep. 3, 2013 (CN) .......................... 2013 1 0395514

(51) Int. Cl.
*A61B 5/00* (2006.01)
*A61C 19/04* (2006.01)
(Continued)

(52) U.S. Cl.
CPC ........... *A61B 5/0051* (2013.01); *A61B 5/1111* (2013.01); *A61C 8/0089* (2013.01);
(Continued)

(58) Field of Classification Search
None
See application file for complete search history.

(56) References Cited

U.S. PATENT DOCUMENTS 3,292,426 A * 12/1966 McCann ................ G21C 17/12
376/245
3,580,056 A * 5/1971 Warner .................. G01H 13/00
324/226

(Continued)

FOREIGN PATENT DOCUMENTS

| CN | 103499644 A | 1/2014 |
| CN | 203772805 U | 8/2014 |

(Continued)

OTHER PUBLICATIONS

Mar. 12, 2015, Written Opinion of the International Searching Authority as to PCT/CN2014/000811.
(Continued)

*Primary Examiner* — Nicholas Lucchesi
*Assistant Examiner* — Shannel Wright
(74) *Attorney, Agent, or Firm* — Mei & Mark LLP

(57) ABSTRACT

The present invention relates to a torsional vibration resonance frequency measuring method and a novel amplitude transformer for assessing the stability of dental implants. In one example, a torsional vibration resonance frequency measuring method includes installing an amplitude transformer on a dental implant, energizing a torsional vibration mode, gathering resonance signals, and analyzing a resonance frequency. In another example, an amplitude transformer for measuring torsional vibration resonance fre-
(Continued)

quency in a dental implant, includes an anti-rotary horizontal double-winged component and a central bolt. The central bolt is configured to closely connect with the inner threads of the dental implant, such that the amplitude transformer can integrate with the dental implant sufficient to vibrate as an integral structure under energizing.

18 Claims, 4 Drawing Sheets

(51) Int. Cl.
    *A61C 8/00*     (2006.01)
    *A61B 5/11*     (2006.01)
    *A61C 1/18*     (2006.01)
    *G01H 13/00*     (2006.01)

(52) U.S. Cl.
    CPC .............. *A61C 19/04* (2013.01); *A61C 1/186* (2013.01); *G01H 13/00* (2013.01)

(56) References Cited

U.S. PATENT DOCUMENTS

| | | | | | |
|---|---|---|---|---|---|
| 3,603,137 | A | * | 9/1971 | Banks | G01N 9/002 73/24.05 |
| 5,392,779 | A | * | 2/1995 | Meredith | A61B 5/1111 600/437 |
| 2002/0143268 | A1 | * | 10/2002 | Meredith | A61B 5/1111 600/552 |
| 2005/0026113 | A1 | * | 2/2005 | Chen | A61B 5/076 433/173 |
| 2007/0270684 | A1 | * | 11/2007 | Cawley | A61C 8/00 600/422 |
| 2008/0199828 | A1 | * | 8/2008 | Pan | A61C 19/04 433/167 |
| 2009/0299173 | A1 | * | 12/2009 | Cawley | A61C 8/00 600/422 |

FOREIGN PATENT DOCUMENTS

| TW | 483750 B | 4/2002 |
|---|---|---|
| TW | 200916059 A | 4/2009 |

OTHER PUBLICATIONS

Oct. 29, 2014, International Search Report for PCT/CN2014/000811.

Zhai, Effects of the Orientation of the Osstell Transducer on Torsional Vibration Behavior of Dental Implants: A Numerical Approach, CMFD, No. 04, Apr. 15, 2012, pp. 16, 19, 26, 30, 39-47, figures 1-10.

Sennerby, Implant Stability Measurements Using Resonance Frequency Analysis: Biological and Biomechanical Aspects and Clinical Implications. Periodontology 2000, vol. 47, Dec. 31, 2008.

Min Zhai, Effects on Torsional Vibration Behavior of Dental Implants: a Numerical Approach, China Master's Theses Full-text Database (CMFD), Medical Science, 4th issue, E074-117 (Apr. 15, 2012).

* cited by examiner

TORSIONAL VIBRATION RESONANCE FREQUENCY MEASUREMENT METHOD FOR ESTIMATING STABILITY OF DENTAL IMPLANT AND NOVEL AMPLITUDE TRANSFORMER

FIELD OF THE INVENTION

The present invention relates to a measuring method for assessing the stability of dental implants in the art of stomatology, and in particular relates to a torsional vibration resonance frequency measuring method for assessing the stability of dental implants and a novel amplitude transformer.

BACKGROUND ART

In the 21st century, due to the improvement of technology and the richness and development of the implantation theory, dental implantation has become a mature clinic technology for partial anodontia repairing. It does not only achieve the recovery of the function of missing teeth, but also restores the aesthetic appearance of natural teeth. As one of the basic elements for a successful implanting, the osseointegration between the dental implants and the surrounding osseous tissue has been the focus and investigation hotspot for a long time. Only when a dental implant reaches an osseointegration with the surrounding alveolar bone can it function to support and fix the prosthesis and perform its normal functions. Different designs of dental implants and different surface modifications on dental implants affect the progress and rate of the osseointegration of the implants, and the ultimate objects of seeking better bone healing speed and osseointegration rate are to shorten the treatment period, increase the bonding strength between the dental implants and the osseous tissue, and improve its stability and supporting capacity. Therefore, the biomechanic assessment on the dental implant/bone interface has became one of the important topics in the study of osseointegration, and, at present, a main research target is to find an study means that can harmlessly and precisely reflect the mechanical behavior, i.e., stability, of the bone-implant interface in the dental implant healing progress, and make a continuous observation possible, that is, an assessing method that is suitable for the clinical research on dental implant osseointegration in order to assess the level of the osseointegration of dental implants in an objective fashion. Resonance frequency analysis, as a mature technique for studying structure object and structural mechanics characteristics, has a potential to provide an effective approach for achieving the above target. That idea was seriously proposed by Meredith and Huang in the 1990s, after which, however, many basic and clinical studies proved that the dental implant resonance frequency analysis method they established cannot precisely and objectively reflect the bone healing progress of the dental implants and the interface bonding characteristic, which results in that the result of a single measurement does not possess practical clinical guiding significance. The underlying cause of the above problem is that Meredith and Huang simply chose the bending vibration mode as the study object when studying the resonance frequency of the dental implants. Although the bending vibration mode has advantages such as the easiness of being triggered and being identified and caught by instruments, it cannot directly reflect the mechanical behavior of the dental implant-bone interface, while torsional vibration is the very mode ideal for revealing the structural characteristic of the dental implant-bone interface.

Taking an overview on the study approach of dental implant osseointegration, besides histologic methods, biomechanic study is one of the important approaches, and is especially more important in clinical research. Many research techniques have emerged on dental implant osseointegration strength and dental implant stability.

Dental implant push-out test and spin-out test are commonly used mechanic study approaches for dental implant osseointegration at present, and as they provide the maximum disruptive strength of the dental implant-bone interface, they are destructive test methods, cannot be used to continuously observe the dental implants over time, and, furthermore, they are not suitable for clinical research. Dental implant percussion is a qualitative examining method for clinically deciding the stability of the dental implants and the presence of osseointegration, but it lacks an objective quantitative criteria. The Periotest mobility meter, invented according to the damping principle, overcomes the shortcomings of subjectivity and qualitativeness of simple percussion of dental implants, by outputting the mobility of dental implants as Periotest values (PTVs), which are generally between −5 and +5. However, the method has a poor repeatability, wherein the operation manner greatly affects the results, and investigation proves that the measured numerical values cannot precisely reflect the biomechanic nature of the bone-implant interface of dental implants.

Objects having masses and structures made up by such objects have their intrinsic frequencies, which are decided by the stiffness of the objects as well as the interfacial stiffness between structures, and when an external energizing frequency overlaps with the intrinsic frequency of an object or a structure interface, resonance occurs. Resonance frequency analysis is already a mature technique for investigating object and structure interface stiffness. It was successfully applied to the investigation on the stiffness of human long bone in the 1990s, and its feasibility for serving as a method for assessing fracture union and osteoporosis has been preliminarily proven. The direct bonding between the dental implant and the osseous tissue is the foundation of its successful working. In the initial stage after the implanting, assimilation happens between the dental implant and the surrounding osseous tissue due to surgery trauma; and in the process of the bone healing, the stiffness of the interface bone and the osseointegration stiffness increase gradually. Experiments indicate that the binding stiffness of the dental implant-bone interface reflects the extent of bone healing. On the basis of the above principle, Meredith et. al. incorporated the resonance frequency analysis technique into the dental implant stability research, and made the first Osstell dental implant resonance frequency analyzer. Its principle of operation (see the schematic representations) is as follows: to secure a L-shaped amplitude transformer to the dental implant with screws, install two miniature piezoceramics transducers on the inside and outside of the amplitude transformer (wherein one of them is used to emit 5-15 KHz continuous sine waves to energize the amplitude transformer-dental implant vibration, and the other one is a receiving transducer for receiving the amplitude and the frequency of the amplitude transformer), record a curve diagram about the frequency and the amplitude by using an analyzer, and obtain the resonance frequency by calculating. What it measures is the resonance frequency of the dental implant at lower order bending vibration mode.

In the system comprising the dental implant, the surrounding jaw and the transducer, the resonance frequency of the dental implant is decided by multiple factors, which generally include the stiffness and mass of the dental implant, the vibration moment arm, the density and structure of the surrounding bone of the dental implant, the shear stiffness of the dental implant-bone interface and so on, and the vibration mode presents multiple modes including bending vibration, vertical vibration, horizontal vibration and torsional vibration. Therefore, the resonance frequency of the dental implant consists of a plurality of frequencies, rather than a single one, and presents multiple stages. Under different vibration modes, the factors that affect the resonance frequency vary, and the mechanical behaviors of the dental implant-jawbone structural system are reflected with emphasis in different aspects. Currently the research on the resonance frequency of dental implant is on the basis of the bending vibration mode of dental implant, and under the mode the resonance frequency is majorly decided by factors such as the structure and mass of the surrounding osseous tissue of the dental implant and the height the dental implant protrudes above the bone surface, and mainly reflects the stability of the dental implant. Due to being influenced by too many factors, the current dental implant resonance frequency analysis method based on the bending vibration mode cannot objectively and precisely reflect the mechanical behavior of the dental implant-bone interface and the osseointegration level, which results in that the result of a single measurement does not possess practical clinical guiding significance; additionally, the connecting location and the arrangement orientation of the transducer largely affects the measurement result, resulting in the doubt on its clinical and scientific application values.

It can be seen that, the afore-said prior art measuring methods of the stability of dental implants still present many defects, and thus urgently need improvement. Given the defects in the prior art stability measuring methods of dental implants, the inventor, based on rich practice experience and expertise, made the present invention by positive innovating, unceasing researching and designing, and repeatedly sample trial making and improving.

BRIEF SUMMARY OF THE INVENTION

The major object of the present invention is to overcome the defects in the prior art measuring method for assessing the stability of dental implants and provide a novel torsional vibration resonance frequency measuring method for assessing the stability of dental implants. The technical problem sought to be solved is to overcome the defects of the poor repeatability and objectivity of the Periotest method and overcome the defects of the poor relation between the Ostell resonance frequency measuring method and dental implant osseointegration in order to increase the repeatability of the measurement result and the relation with the dental implant osseointegration progress and improve the practicality.

Another object of the present invention is to overcome the defects of the prior art amplitude transformers and thus provide a novel amplitude transformer with a new structure. The technical problem sought to be solved is to measure the resonance frequency under the torsional vibration mode, and by taking advantage of the relation between the resonance frequency and the stiffness of the bone of the bone-implant interface surrounding the dental implant under the mode, increase the objectivity of the measurement result about the dental implant stability determining, avoid the mixed influence from non-osseointegration-related factors, increase sensibility to dental implant bone healing, and improve practicality.

The present invention aims to, beginning from the torsional vibration mode of dental implants, according to the principle that tangential energizing triggers torsional vibration mode, study the amplitude transformer design ideal for energizing torsional vibration mode by using three-dimensional finite element method; establish a resonance frequency analysis method for torsional vibration mode of dental implants by referring to Meredith's flexural resonance frequency measurement technique principle; and reveal the correlativity between the resonance frequency of torsional vibration and dental implant osseointegration by using three-dimensional finite element, in-vitro model experiment and animal experiment study. The present invention will provide an effective novel assessing method for the clinical research on dental implant osseointegration. Not only it will provide an important assessing indicator for studying dental implant osseointegration and optimizing dental implant performance and has an important scientific research value, but also it will provide a clinical assessment approach for judging whether or not the dental implanting is successful and deciding the right time for dental implant repairing and has an important clinical application value.

The objectives of the present invention can be achieved and the technical problems can be solved by adopting the following technical solutions. A torsional vibration resonance frequency measuring method for assessing the stability of dental implants and a novel amplitude transformer in the present invention comprises the following steps:

Step 1: Installing a Novel Amplitude Transformer:

installing a novel amplitude transformer having a double-winged, horizontal, symmetrical and vertical structure for measuring resonance frequency onto a dental implant 3, by applying a central bolt 2 of the novel amplitude transformer to tightly fasten the novel amplitude transformer onto the surface of the dental implant 3, with a torque force of 3 to 10 N·cm to fasten the central bolt 2 of the novel amplitude transformer, so as to tightly fasten the two, thus forming a dental implant-amplitude transformer system;

Step 2: Energizing a Torsional Vibration Mode in the dental implant-amplitude transformer system, energizing either unilateral side or bilateral sides of the bilateral horizontal wings of the novel amplitude transformer by a contact or non-contact method, and energizing the dental implant in a tangential direction to make torsional vibration as a main vibration mode of the dental implant-amplitude transformer system;

Step 3: Gathering Resonance Signals:

recording vibration frequencies and amplitudes of the novel amplitude transformer by applying an electromagnetic signal receiver; and Step 4: Analyzing Resonance Frequencies:

gathering and processing data, plotting an amplitude-frequency curve diagram, and calculating the torsional resonance frequency according to the torsional vibration mode, which is the main vibration peak.

In the afore-said torsional vibration resonance frequency measuring method for assessing the stability of dental implants, the most preferred torque force of the central bolt for fastening the novel amplitude transformer is 4 to 6 N·cm.

In the afore-said torsional vibration resonance frequency measuring method for assessing the stability of dental implants, the contact or non-contact method in the dental implant-amplitude transformer system is knock or electromagneticly energizing either the unilateral side or bilateral sides of the bilateral horizontal wings of the novel amplitude transformer, wherein when electromagnetic signal is the energizing source, the frequency ranges from 0-20000 hertz.

In the afore-said torsional vibration resonance frequency measuring method for assessing the stability of dental implants, the action point of said energizing applied to unilateral side or bilateral sides of the bilateral horizontal wings of the novel amplitude transformer is located at a distal end of the bilateral horizontal wings, perpendicular to the bilateral horizontal wings of the novel amplitude transformer, and tangent to the axial direction of the dental implant.

The object of the present invention can also be achieved and the technical problems can also be solved by adopting the following technical solutions. The novel amplitude transformer for implementing the torsional vibration resonance frequency measuring method for assessing the stability of dental implants comprise an anti-rotary horizontal double-winged component and a central bolt, wherein the anti-rotary horizontal double-winged component is an integrated horizontal, symmetrical and upright structure with two wings composed by bilateral horizontal wings, a middle pillar and an anti-rotary part, wherein the bilateral horizontal wings have two horizontal wings horizontally stretching outward individually from two sides of the top of the middle pillar along the direction parallel to the end surface of the implant neck, symmetrical with the central axis of the middle pillar and perpendicular to the upper end surface of implant neck as a vertical structure; and the middle pillar is provided with a through hole inside it, and the anti-rotary part is at the bottom which matches the inner structure of the top of the neck of the to-be-measured dental implant so that they can be closely occluded with each other with completely meshing limitation; and the said central bolt goes through the through hole of the middle pillar and closely connects with the inner threads of the dental implant, so as to fasten the novel amplitude transformer closely onto the dental implant, forming a dental implant-amplitude transformer system integrating the novel amplitude transformer with the dental implant, and thus the dental implant-amplitude transformer system which integrates the novel amplitude transformer with the dental implant can vibrate as an integral structure under energizing.

In the afore-said novel amplitude transformer, the said anti-rotary part is designed with a conical surface or a concave surface, wherein the concial surface or the concave surface is an anti-rotary structure shaped as a hexagon, octagon or trefoil, the shape of which matches the inner structure of the top of the neck of the to-be-measured dental implant.

In the novel amplitude transformer, the total length of the bilateral horizontal wings from the distal end of the horizontal wing on one side to the distal end of the horizontal wing on the other side in the horizontal direction is from 10 mm to 30 mm, the thickness of the bilateral horizontal wings is from 0.5 mm to 3 mm, and the height of the bilateral horizontal wings is from 3 mm to 10 mm, wherein the most preferred total length of the bilateral horizontal wings is from 15 mm to 20 mm, the most preferred thickness of the bilateral horizontal wings is from 1.3 mm to 1.6 mm, and the most preferred height of the bilateral horizontal wings is from 3 mm to 6 mm.

The materials used by the afore-said novel amplitude transformer includes aluminum alloy, pure titanium, titanium alloy and medical stainless steel, among which aluminum alloy is the most preferred material.

The present invention has at least the following advantages over the prior art:

1. Applying a force on dental implants in the tangential direction is one of the effective approaches for energizing its torsional vibration; the structure design of the novel vertical double-winged amplitude transformer of the present invention facilitates the tangential energizing of dental implants; and by effective energizing, the torsional vibration mode of dental implants can be transferred into mainly vibration mode, which facilitates signal acquisition.

2. Compared with the prior art that uses the flexural resonance frequency of dental implants as the technical principle, by measuring torsional resonance frequency, the present invention can more directly reflect the medium and binding stiffness of the dental implant-bone interface, avoid the influence from non-osseointegration-related factors, and increase the assessing sensibility of dental implant osseointegration and stability.

3. The bone healing of dental implants in terms of mechanical behavior presents in the form that the mechanic stiffness of osseous tissue keeps increasing, and the present invention can more sensitively reflect the extent of dental implant bone healing while monitoring dental implant stability, by which the right time for repairing the dental implants can be guided, and, furthermore, provide a novel approach for studying dental implant osseointegration.

The above description is only a brief summary of the technical solution of the present invention. In order to clarify the technical means of the present invention so that they can be implemented according to the content of the description, and in order to make the above and other objects, features and advantages of the present invention easier to understand, the present invention will now be described in detail by referring to preferred examples and accompanying figures.

wherein:

| 1: an anti-rotary horizontal bilateral wing component | 11: bilateral horizontal wing |
|---|---|
| 12: central standing pillar | 13: an anti-rotary part |
| 2: central bolt | 3: dental implant |

DETAILED DESCRIPTION OF SPECIFIC EMBODIMENTS

The drawings accompanying this specification as listed below, as well as the preferred embodiments, are to further illustrate the technical methods and functions for achieving the predetermined objects in the present invention. The present invention relates to a torsional vibration resonance frequency measuring method for assessing the stability of dental implants and a novel amplitude transformer, on the basis of the multistage resonance frequency attributes which is the inherent attributes of objects, with a designed structure of the novel amplitude transformer, to realize the energizing of the dental implant-amplitude transformer system in a tangential direction to vibrate the system itself to make torsional vibration as a main vibration mode of the system, measuring the torsional resonance frequency of the dental implant by gathering resonance signals and analyzing resonance frequencies. When directly knocking or applying electromagnetic signal to act on the distal end of the horizontal wings of the transformer, it can realize the tangential energizing of the dental implant-amplitude transformer, in which unilateral or bilateral synchronic energizing can achieve the same torsional vibration energizing effect. The specific application methods and steps are as follows.

Embodiment 1

Figure 1A:
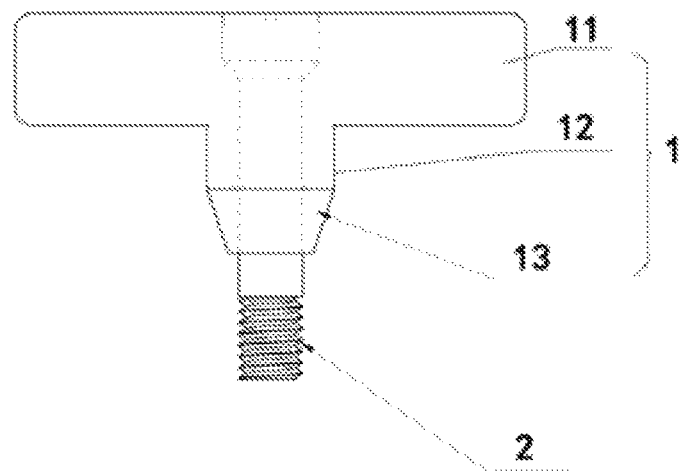
FIG. 1A is a schematic diagram of the main view of the novel amplitude transformer of the present invention.
Figure 1B:
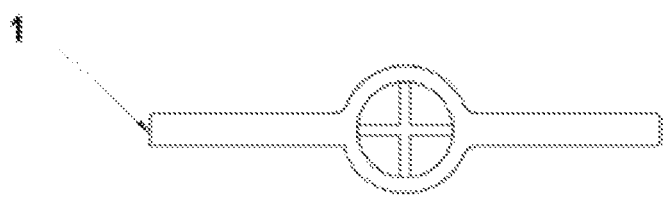
FIG. 1B is a schematic diagram of the top view of the novel amplitude transformer of the present invention.
Figure 1C:
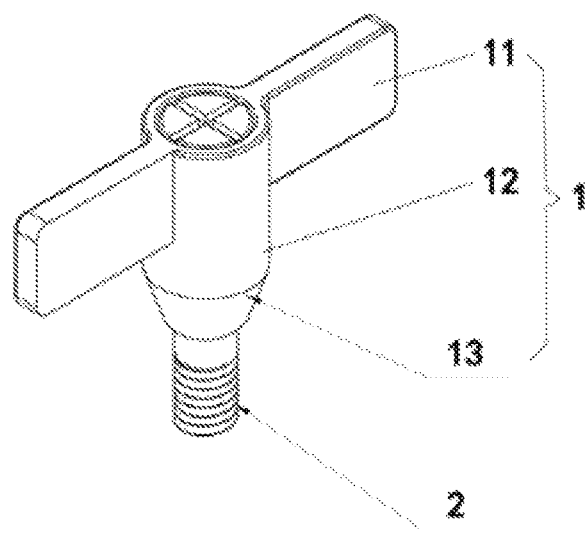
FIG. 1C is a three-dimensional diagram of the appearance of the novel amplitude transformer of the present invention.
Figure 2:
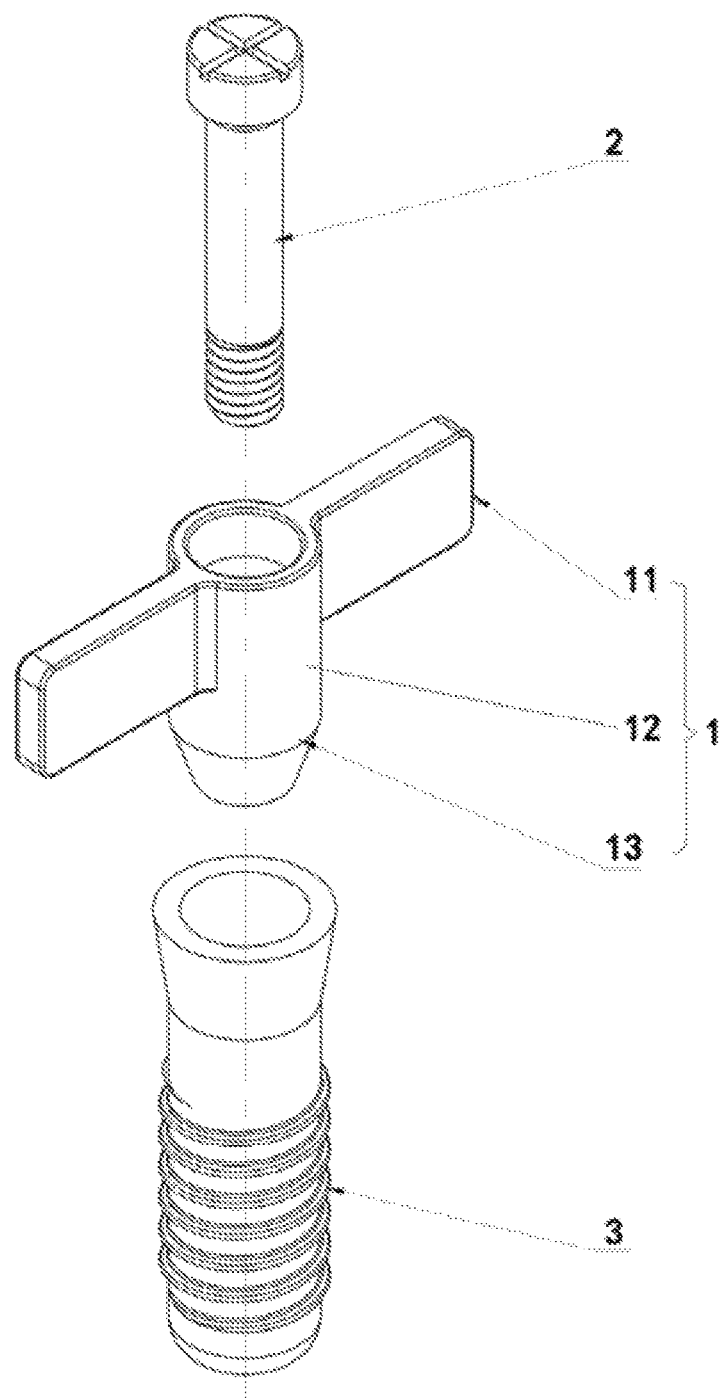
FIG. 2 is a exploded three-dimensional diagram of the novel amplitude transformer of the present invention.
Figure 3:
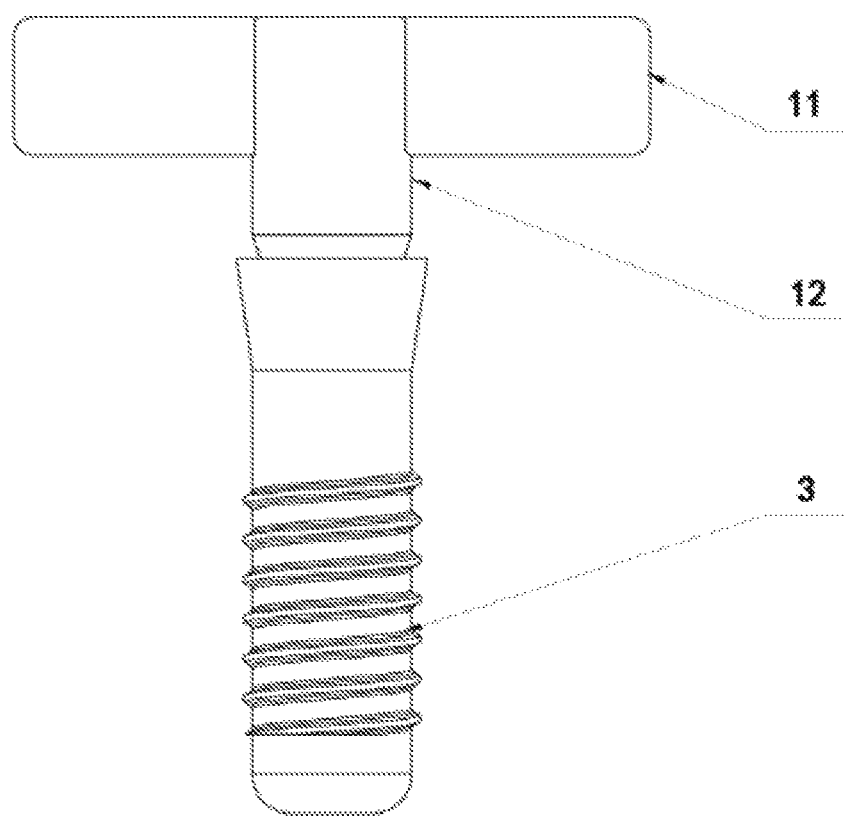
FIG. 3 is an assembly diagram of the novel amplitude transformer and the dental implant of the present invention.
Figure 4:
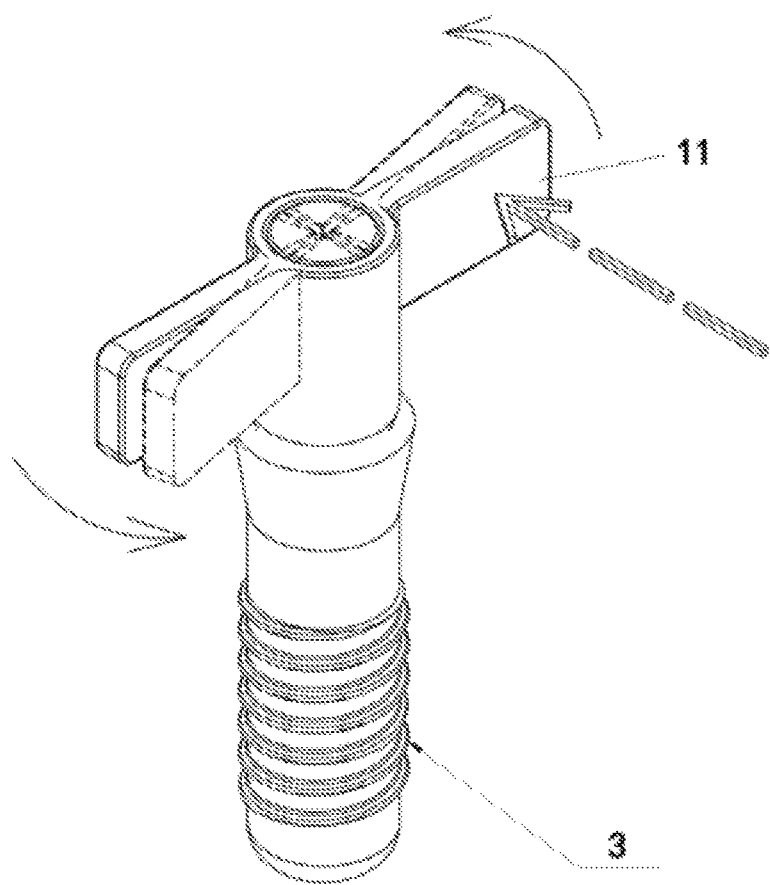
FIG. 4 is a diagram of the torsional vibration of the novel amplitude transformer and the dental implant of the present invention.

In FIG. 4, it shows the preferred embodiment example of the present invention which is the torsional vibration resonance frequency measuring method for assessing the stability of dental implants and a novel amplitude transformer, mainly comprising the following steps:

Step 1: Installing a Novel Amplitude Transformer:

installing a novel amplitude transformer having a double-winged, horizontal, symmetrical and vertical structure for measuring resonance frequency onto a dental implant 3, by applying a central bolt 2 of the novel amplitude transformer to tightly fasten the novel amplitude transformer onto the surface of the dental implant 3, with a torque force of 3 to 10 N·cm to fasten the central bolt 2 of the novel amplitude transformer, so as to tightly fasten the two, thus forming a dental implant-amplitude transformer system, wherein the most preferred torque force of the central bolt for fastening the novel amplitude transformer is 4 to 6 N·cm. The torque force used in the present embodiment is 5 N·cm;

Step 2: Energizing a Torsional Vibration Mode:

in the dental implant-amplitude transformer system, energizing unilateral side or bilateral sides of the bilateral horizontal wings 11 of the novel amplitude transformer by a contact or non-contact method, and energizing the dental implant 3 in a tangential direction to make torsional vibration as the main vibration mode of the dental implant-amplitude transformer system;

wherein in the present invention, the contact method is knocking, and the action point of said energizing applied to the unilateral side or bilateral sides of the bilateral horizontal wings 11 of the novel amplitude transformer is located at a distal end of the bilateral horizontal wings 11, perpendicular to the bilateral horizontal wings 11 of the novel amplitude transformer and tangent to the axial direction of the dental implant 3 which is to be measured;

Step 3: Gathering Resonance Signals:

recording vibration frequencies and amplitudes of the novel amplitude transformer by applying an electromagnetic signal receiver; and Step 4: Analyzing Resonance Frequencies:

gathering and processing data, plotting an amplitude-frequency curve diagram, and calculating the torsional resonance frequency according to the torsional vibration mode which is the main vibration peak, wherein the torsional vibration resonance frequency value is positively correlated to the stability of the dental implant 3 and the degree of bone healing of the dental implant 3.

Embodiment 2

The torque force of the central bolt 2 for fastening the novel amplitude transformer is 5 N·cm. In the novel amplitude transformer system, the non-contact energizing method is applied to electromagneticly energize the unilateral side or bilateral sides of the bilateral horizontal wings 11, wherein when the electromagnetic signal is the energizing source, the frequency ranges from 0-20000 hertz. In the present embodiment, micro piezoelectric ceramic is used as the energizing source to synchronically apply to the bilateral horizontal wings 11 in the same rotation direction. Other steps are the same with those mentioned in embodiment 1.

Embodiment 3

As shown in FIG. 1, FIG. 2, FIG. 3, and FIG. 4, the novel amplitude transformer of the preferred embodiment in the present invention mainly includes an anti-rotary horizontal bilateral wing component 1 and a central bolt 2, wherein the anti-rotary horizontal double-winged component 1 is an integrated horizontal, symmetrical and upright structure with two wings composed by bilateral horizontal wing 11; a central standing pillar 12; and an anti-rotary part 13, wherein the bilateral horizontal wing 11 has two horizontal wings, which horizontally stretching outward individually from two sides of the top of the central standing pillar 12 along the direction parallel to the end surface of the neck of dental implant 3, symmetrical with the central axis of the central standing pillar 12 and perpendicular to the upper end surface of implant neck as a vertical structure; wherein the central standing pillar 12 is provided with a through hole inside it, and the anti-rotary part 13 is at the bottom which matches the inner structure on top of the neck of the to-be-measured dental implant so that the they can be closely occluded with each other with complete meshing limitation; and the said central bolt 2 goes through the through hole of the central standing pillar 12 and closely connects with the internal threads of the dental implant 3, so as to fasten the novel amplitude transformer closely onto the dental implant 3, forming a dental implant-amplitude transformer system integrating the novel amplitude transformer with the dental implant 3, and thus the dental implant-amplitude transformer system integrates the novel amplitude transformer with the dental implant 3 can vibrate as an integral structure under energizing.

The said anti-rotary part 13 is designed with a conical surface or a concave surface, wherein the conical surface or the concave surface is an anti-rotary structure shaped as a hexagon, octagon or trefoil, the shape of which matches the inner structure on top of the neck of the to-be-measured dental implant 3 so that they can realize complete meshing limitation.

The anti-rotary part 13 of the present embodiment is in the shape of an anti-rotary conical surface, which matches the inner structure on top of the neck of the to-be-measured dental implant 3 so that the they can realize complete meshing limitation. In the present embodiment, the anti-rotary conical surface is with a hexagon, octagon or trefoil shaped anti-rotary structure. The said central bolt 2 goes through the through hole of the anti-rotary part 13 and connects with the internal threads of the dental implant 3, so as to fasten the novel amplitude transformer closely onto the dental implant 3, thus forming a dental implant-amplitude transformer system integrating the novel amplitude transformer with the dental implant 3, and thus the dental implant-amplitude transformer system which integrates the novel amplitude transformer with the dental implant 3 can vibrate as an integral structure under energizing.

The total length of the bilateral horizontal wing 11 from the distal end of the horizontal wing on one side to the distal end of the horizontal wing on the other side in the horizontal direction is from 10 mm to 30 mm, the thickness of the bilateral horizontal wings 11 is from 0.5 mm to 3 mm, and the height of the bilateral horizontal wing is from 3 mm to 10 mm, wherein the most preferred total length of the bilateral horizontal wings 11 is from 15 mm to 20 mm, the most preferred thickness of the bilateral horizontal wings 11 is from 1.3 mm to 1.6 mm, and the most preferred height of the bilateral horizontal wings 11 is from 3 mm to 6 mm.

The materials used by the novel amplitude transformer include aluminum alloy, pure titanium, titanium alloy and medical stainless steel, among which aluminum alloy is the most preferred material. In the present embodiment, the material used is aluminum alloy.

The said anti-rotary part 13 is designed with an anti-rotary concave surface, wherein the conical surface or the concave surface is an anti-rotary structure shaped as a hexagon, octagon, or trefoil shaped anti-rotary structure, the shape of which matches the inner structure on top of the neck of the to-be-measured dental implant 3 so that the they can realize complete meshing limitation.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

What is claimed is:

1. A torsional vibration resonance frequency measuring method for assessing the stability of a dental implant, comprising:
    installing an amplitude transformer on the dental implant;
    energizing a torsional vibration mode in a system comprising the dental implant and the installed amplitude transformer;
    gathering the resonance signals; and
    analyzing a resonance frequency.

2. The torsional vibration resonance frequency measuring method of claim 1, wherein:
    installing the amplitude transformer comprises tightly fastening the amplitude transformer on the dental implant with a torque force of 3 to 10 N·cm via a central bolt to form a dental implant-amplitude transformer system;
    energizing the torsional vibration mode comprises energizing a unilateral side or bilateral sides of bilateral horizontal wings of the amplitude transformer, and energizing the dental implant in a tangential direction to make torsional vibration a main vibration mode of the dental implant-amplitude transformer system;
    gathering the resonance signals comprises recording vibration frequencies and amplitudes of the amplitude transformer by an electromagnetic signal receiver; and
    analyzing the resonance frequency comprises processing the recorded vibration frequencies and amplitudes, plotting an amplitude-frequency curve diagram, and calculating the torsional resonance frequency according to the torsional vibration mode.

3. The torsional vibration resonance frequency measuring method of claim 2, wherein tightly fastening the amplitude transformer further comprises using a torque force of 4 to 6 N·cm via the central bolt to form the dental implant-amplitude transformer system.

4. The torsional vibration resonance frequency measuring method of claim 2, wherein:
    energizing the unilateral side or the bilateral sides of the bilateral horizontal wings of the amplitude transformer comprises directly knocking or electromagnetically energizing via an electromagnetic signal; and
    if the amplitude transformer is electromagnetically energized, a frequency of the electromagnetic signal is in the range of 0-20000 hertz.

5. The torsional vibration resonance frequency measuring method of claim 3, wherein:
    energizing the unilateral side or the bilateral sides of the bilateral horizontal wings of the amplitude transformer comprises directly knocking or electromagnetically energizing via an electromagnetic signal; and
    if the amplitude transformer is electromagnetically energized, a frequency of the electromagnetic signal ranges from 0-20000 hertz.

6. The torsional vibration resonance frequency measuring method of claim 4, wherein:
    energizing the unilateral side or the bilateral sides of the bilateral horizontal wings of the amplitude transformer occurs at an action point located at a distal end of the bilateral horizontal wings, perpendicular to the bilateral horizontal wings, and tangential to an axial direction of the dental implant.

7. The torsional vibration resonance frequency measuring method of claim 5, wherein:
    energizing the unilateral side or the bilateral sides of the bilateral horizontal wings of the amplitude transformer occurs at an action point located at a distal end of the bilateral horizontal wings, perpendicular to the bilateral horizontal wings, and tangential to an axial direction of the dental implant.

8. The torsional vibration resonance frequency measuring method of claim 1, wherein installing the amplitude transformer comprises tightly fastening the amplitude transformer on the dental implant with a torque force of 3 to 10 N·cm via a central bolt to form a dental implant-amplitude transformer system.

9. The torsional vibration resonance frequency measuring method of claim 1, wherein energizing the torsional vibration mode comprises energizing a unilateral side or bilateral sides of bilateral horizontal wings of the amplitude transformer, and energizing the dental implant in a tangential direction to make torsional vibration a main vibration mode of the dental implant-amplitude transformer system.

10. The torsional vibration resonance frequency measuring method of claim 1, wherein gathering the resonance signals comprises recording vibration frequencies and amplitudes of the amplitude transformer by an electromagnetic signal receiver.

11. The torsional vibration resonance frequency measuring method of claim 1, wherein analyzing the resonance frequency comprises processing the recorded vibration frequencies and amplitudes, plotting an amplitude-frequency curve diagram, and calculating the torsional resonance frequency according to the torsional vibration mode.

12. The torsional vibration resonance frequency measuring method of claim 8 wherein tightly fastening the amplitude transformer further comprises using a torque force of 4 to 6 N·cm via the central bolt to form the dental implant-amplitude transformer system.

13. The torsional vibration resonance frequency measuring method of claim 9, wherein energizing the unilateral side or the bilateral sides of the bilateral horizontal wings of the amplitude transformer comprises directly knocking.

14. The torsional vibration resonance frequency measuring method of claim 9, wherein energizing the unilateral side or the bilateral sides of the bilateral horizontal wings of the amplitude transformer comprises electromagnetically energizing via an electromagnetic signal.

15. The torsional vibration resonance frequency measuring method of claim 9, wherein energizing the unilateral side or the bilateral sides of the bilateral horizontal wings of the amplitude transformer comprises electromagnetically energizing via an electromagnetic signal in the range of 0-20000 hertz.

16. The torsional vibration resonance frequency measuring method of claim 13, wherein energizing the unilateral side or the bilateral sides of the bilateral horizontal wings of the amplitude transformer occurs at an action point located at a distal end of the bilateral horizontal wings, perpendicular to the bilateral horizontal wings, and tangential to an axial direction of the dental implant.

17. The torsional vibration resonance frequency measuring method of claim 14, wherein energizing the unilateral side or the bilateral sides of the bilateral horizontal wings of the amplitude transformer occurs at an action point located at a distal end of the bilateral horizontal wings, perpendicular to the bilateral horizontal wings, and tangential to an axial direction of the dental implant.

18. The torsional vibration resonance frequency measuring method of claim 15, wherein energizing the unilateral side or the bilateral sides of the bilateral horizontal wings of the amplitude transformer occurs at an action point located at a distal end of the bilateral horizontal wings, perpendicular to the bilateral horizontal wings, and tangential to an axial direction of the dental implant.

\* \* \* \* \*